(12) United States Patent  (10) Patent No.: US 8,540,690 B2
Nomoto et al.  (45) Date of Patent: Sep. 24, 2013

(54) ABSORBENT ARTICLE

(75) Inventors: Takashi Nomoto, Kagawa (JP); Akiyasu Nagata, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 13/262,320

(22) PCT Filed: Sep. 18, 2009

(86) PCT No.: PCT/JP2009/066845
§ 371 (c)(1),
(2), (4) Date: Sep. 30, 2011

(87) PCT Pub. No.: WO2010/113338
PCT Pub. Date: Oct. 7, 2010

(65) Prior Publication Data
US 2012/0022483 A1   Jan. 26, 2012

(30) Foreign Application Priority Data
Mar. 31, 2009 (JP) ................................ 2009-087152

(51) Int. Cl.
*A61F 13/15* (2006.01)
*A61F 13/20* (2006.01)

(52) U.S. Cl.
USPC ............. 604/385.04; 604/385.01; 604/385.03

(58) Field of Classification Search
USPC ..................... 604/385.01, 385.03, 385.04
See application file for complete search history.

(56) References Cited

U.S. PATENT DOCUMENTS

| 5,478,336 A | 12/1995 | Pigneul |
| 5,788,686 A | 8/1998 | Ahr et al. |
| 6,843,785 B2 * | 1/2005 | Hammonds et al. ...... 604/385.05 |
| 2007/0055212 A1 * | 3/2007 | Kameo et al. ............ 604/385.04 |

FOREIGN PATENT DOCUMENTS

| EP | 0347319 A1 | 12/1989 |
| EP | 05111905 A1 | 11/1992 |
| JP | 54-168798 Y | 11/1979 |
| JP | 6-38953 Y | 5/1994 |
| JP | 9-512454 A | 12/1997 |

(Continued)

OTHER PUBLICATIONS

International Search Report from corresponding PCT application No. PCT/JP2009/066845 dated Dec. 22, 2009, 2 pgs.

(Continued)

*Primary Examiner* — Elizabeth Houston
*Assistant Examiner* — Aundria Hairell
(74) *Attorney, Agent, or Firm* — Brinks Hofer Gilson & Lione

(57) ABSTRACT

A sanitary napkin comprises an absorbing body. The absorbing body includes a fluid-permeable top sheet, a fluid-impermeable back sheet, and an absorber arranged between the top sheet and the back sheet. The napkin comprises a cover sheet for covering the surface of the top sheet. A circumferential edge region of the cover sheet is joined to the absorbing body. A plurality of flaps for fixing the absorbing body to underwear are sectionalized by a sectionalizing line in the central region of the cover sheet. At the time of use, the flaps are folded in the folding regions and are expanded so as to be fixed to the underwear. The flaps include a front flat and a rear flap that expand in the back-and-forth direction, and a left flap and a right flap that expand in the right-and-left direction.

11 Claims, 8 Drawing Sheets

(56) References Cited

FOREIGN PATENT DOCUMENTS

| JP | H 11-113959 A | 4/1999 |
|----|---------------|--------|
| JP | 2001-046425 A | 2/2001 |
| JP | 2002-330992   | 11/2002 |
| JP | 2008188181 A  | 8/2008 |
| JP | 2008-295478 A | 12/2008 |

OTHER PUBLICATIONS

Chinese Office Action from corresponding Chinese application No. 200980158510.9 dated Mar. 27, 2013, (7 pgs.).

* cited by examiner

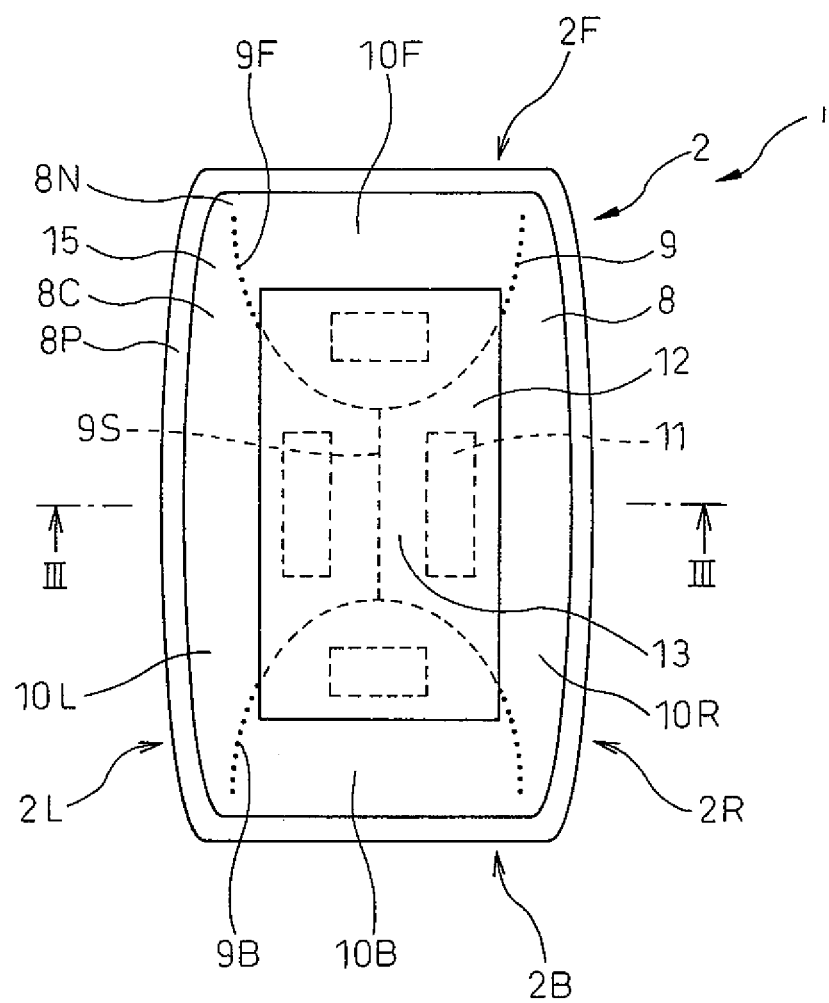

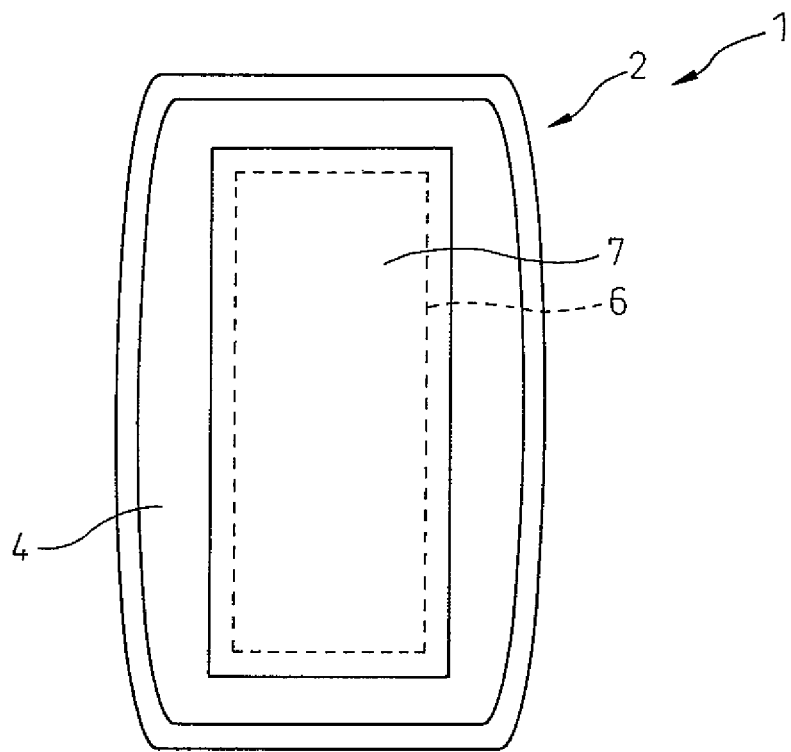
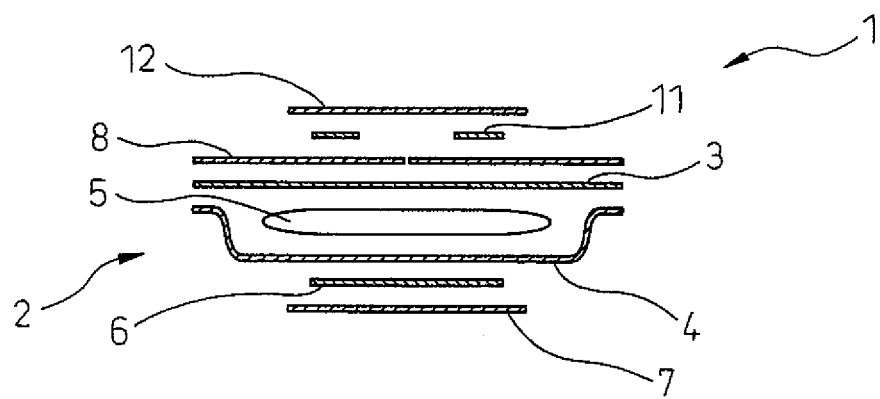

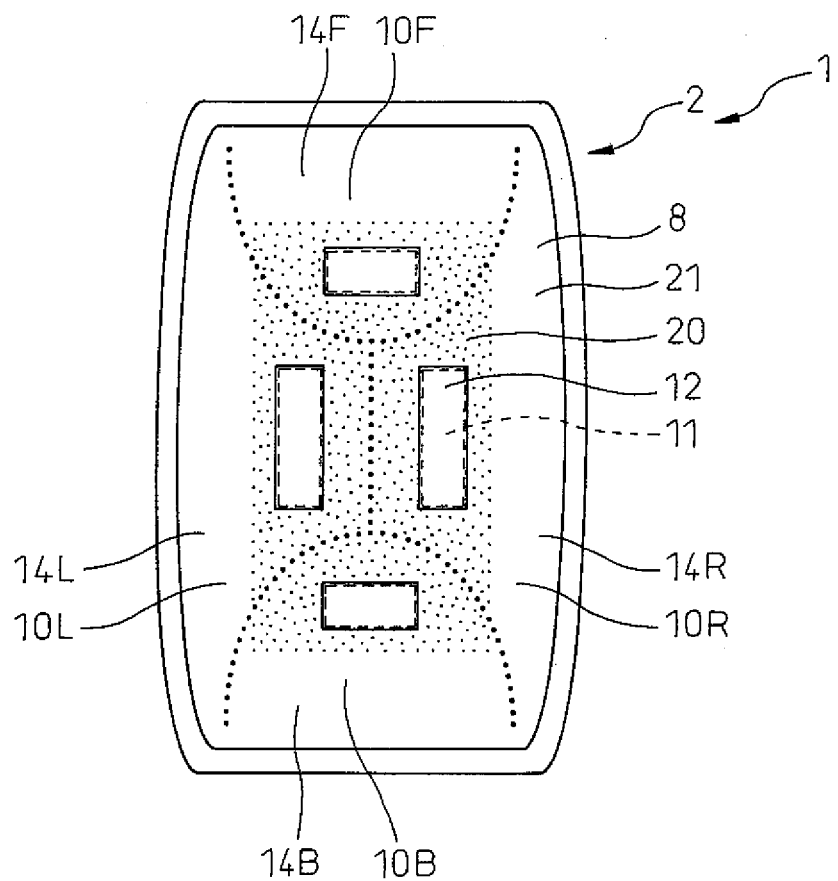

ABSORBENT ARTICLE

RELATED APPLICATION

This application is a 35 U.S.C. §371 national phase filing of International Patent Application No. PCT/JP2009/066845, filed Sep. 18, 2009, through which and to which priority is claimed under 35 U.S.C. §119 to Japanese Patent Application No. 2009-087152, filed Mar. 31, 2009.

TECHNICAL FIELD

This invention relates to an absorbent article.

BACKGROUND ART

There has been known an absorbent article having an absorbing body. The absorbing body includes a fluid-permeable top sheet, a fluid-impermeable back sheet, and an absorber arranged between the top sheet and the back sheet. A cover sheet covering the surface of the top sheet has a pair of flaps sectionalized by a weakened line for fixing the absorbing body to clothing. At the time of use, the pair of flaps are folded and expanded so as to be fixed to the clothing (see PTL1). In an embodiment of PTL1 shown in FIGS. 1 to 4 thereof, provision is made for a pair of flaps that are expanded in the right-and-left direction and in the embodiment shown in FIG. 5 thereof, provision is made for a pair of flaps that are expanded in the back-and-forth direction.

CITATION LIST

Patent Literature

PTL1 JP-T-9-512454

SUMMARY OF INVENTION

Technical Problem

However, it is difficult to fix the absorbing body to clothing by only using a pair of flaps. As a result, the absorbing body may undergo twisting or deviation in position, and the absorbed fluid, such as menses blood or urine may leak.

Solution to Problems

In order to solve the above problem, according to the present invention, there is provided an absorbent article comprising an absorbing body, the absorbing body including a fluid-permeable top sheet, a fluid-impermeable back sheet, and an absorber arranged between the top sheet and the back sheet, wherein the absorbent article further comprises a cover sheet for covering the surface of the top sheet, wherein a circumferential edge region of the cover sheet is joined to the absorbing body, and, in the central region of the cover sheet, at least three flaps for fixing the absorbing body to clothing are sectionalized by a sectionalizing line which is constituted by a weakened line or a cut line, and wherein, at the time of use, the flaps are folded in the folding regions and are expanded so as to be fixed to the clothing.

Advantageous Effect of Invention

The absorbing body can be reliably fixed to clothing.

BRIEF DESCRIPTION OF DRAWINGS

FIG. 1 is a front view of a sanitary napkin.
FIG. 2 is a back view of the sanitary napkin.
FIG. 3 is a schematic transverse sectional view of the sanitary napkin along the line in FIG. 1.
FIG. 7 is a front view of the sanitary napkin according to another embodiment of the invention.

DESCRIPTION OF EMBODIMENTS

Figure 4:
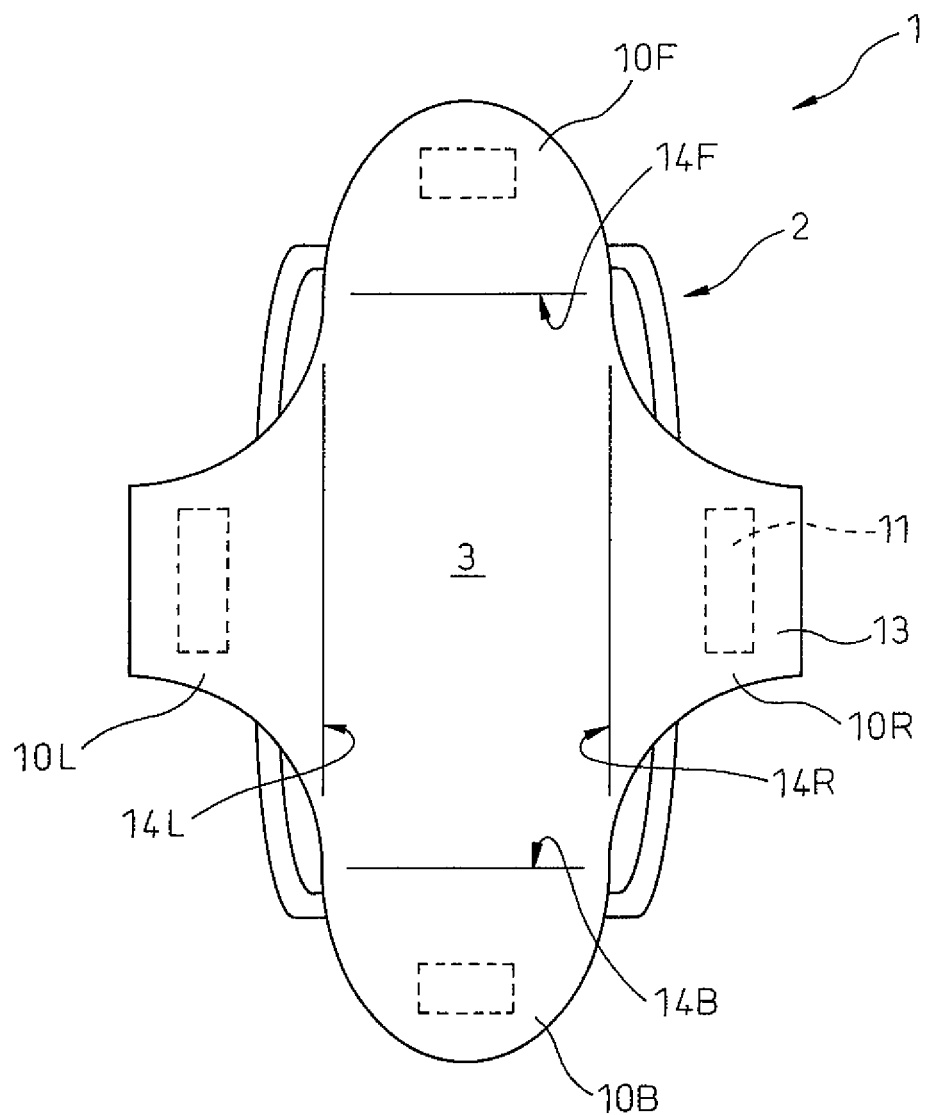
FIG. 4 is a front view of the sanitary napkin with the flaps being expanded.

FIGS. 1 to 3 illustrate a case where the invention is applied to a sanitary napkin. However, the invention can be, further, applied to other absorbent articles such as a panty liner, incontinence pad and the like.

Referring to FIGS. 1 to 3, the sanitary napkin (hereinafter also referred to simply as "napkin") 1 according to the embodiment of the invention includes an absorbing body 2. The absorbing body 2 includes a fluid-permeable top sheet 3, a fluid-impermeable back sheet 4 and an absorber 5 capable of holding fluid being arranged between the top sheet 3 and the back sheet 4. The top sheet 3 and the back sheet 4 are substantially of the same size, and are joined together along the circumferential edges thereof by hot-melt adhesion or heat-sealing. Further, a sticking portion 6 is joined to the surface of the back sheet 4 that, in use, faces the clothing such as underwear so that the absorbing body 2 can be fixed to the underwear. The sticking portion 6 is covered with a protection sheet 7.

In FIG. 1, reference numerals 2F, 2B, 2L and 2R denote a front edge, a rear edge, a left side edge and a right side edge of the napkin 1 or the absorbing body 2. The front, rear, left and right are corresponding to the front, rear, left and right of the body of the user at the time of use.

The surface of the top sheet 3 that comes in contact with the user's skin at the time of use is covered with a fluid-impermeable cover sheet 8. The cover sheet 8 is substantially of the same size as the absorbing body 2, and therefore, covers substantially the entire surface of the top sheet 3. Further, the cover sheet 8 is joined to the top sheet 3 or the absorbing body 2 along its annular circumferential edge region 8P by hot-melt adhesion or heat-sealing. On the other hand, a central region 8C other than the circumferential edge region 8P is not joined to the top sheet 3.

A sectionalizing line 9 such as a perforated weakened line is formed in advance in the central region 8C of the cover sheet 8, and a plurality of flaps are sectionalized or formed in the central region 8C by the sectionalizing line 9 to fix the absorbing body 2 to the underwear. The sectionalizing line 9 may be constituted by a cut line that completely cuts the cover sheet 8.

In the embodiment of the invention, the sectionalizing line 9 is constituted by a U-shaped curved portion 9F that expands toward the front edge 2F, a U-shaped curved portion 9B that expands toward the rear edge 2B, and a linear portion 9S that connects together the vertexes of the curved portions 9F and 9B substantially at the center of the cover sheet 8. Therefore, in the central region 8C, there are sectionalized four flaps, i.e., a semi-elliptical front flap 10F and rear flap 10B having curved ends, and a trapezoidal left flap 10L and right flap 10R. In this case, the front and rear flaps 10F and 10B are positioned symmetrically to each other, and the left and right flaps 10L and 10R are positioned symmetrically to each other, too.

The sectionalizing line 9, in this case, is not reaching the circumferential edge region 8P, and therefore non-cut regions 8N are formed between the ends of the sectionalizing line 9 and the circumferential edge region 8P.

Sticking portions 11 are joined to the surfaces of these flaps 10F, 10B, 10L and 10R to fix the corresponding flaps 10F, 10B, 10L and 10R to the underwear. The sticking portions 11 are covered with a common protective sheet. In this case, the sticking portions 11 are joined to the flaps 10F, 10B, 10L and 10R being separated away from the sectionalizing line 9. Therefore, non-sticking regions 13 are formed on the flaps 10F, 10B, 10L and 10R surrounding the sticking portions 11.

Next, the materials of the elements will be described.

The top sheet 3 is constituted by, for example, a porous or nonporous nonwoven fabric or a porous plastic sheet.

The back sheet 4 is constituted by, for example, a hydrophobic nonwoven fabric, a water-impermeable plastic film, a laminated sheet of a nonwoven fabric and a water-impermeable plastic film, a highly water resistant melt-blown nonwoven fabric, or an SMS nonwoven fabric sandwiched by spun-bonded nonwoven fabrics having a large strength.

The absorber 5 is constituted by, for example, a fluffy pulp or an air-laid nonwoven fabric and a highly absorbent polymer. The fluffy pulp is constituted by artificial cellulose fiber, such as chemical pulp, cellulose fiber, rayon or acetate, while the air-laid nonwoven fabric is constituted by a nonwoven fabric obtained by, for example, melt-adhering the pulp and the synthetic fiber together or by fixing them together with a binder, and the highly absorbent polymer is constituted by, for example, a granular or fibrous polymer of the type of starch, acrylic acid or amino acid.

The sticking portions 6 and 11 are constituted by a hot-melt adhesive such as styrene/isoprene/styrene block copolymer (SIS), styrene/butadiene/styrene block copolymer (SBS) or styrene/ethylene/butylene/ethylene copolymer (SEBS).

The cover sheet 8 is constituted by, for example, a hydrophobic nonwoven fabric, a water-impermeable plastic film, a laminated sheet of a nonwoven fabric and a water-impermeable plastic film, a highly water resistant melt-blown nonwoven fabric, or an SMS nonwoven fabric sandwiched by spun-bonded nonwoven fabrics having a large strength, and is, preferably, constituted by the hydrophobic nonwoven fabric. The basis weight of the cover sheet 8 is, preferably, from 15 $g/m^2$ to 60 $g/m^2$. When the cover sheet is constituted by using the plastic film, it is desired that the plastic film has a draping length of 20 mm to 100 mm and, more preferably, 30 mm to 70 mm relying on a cantilever method. If the draping length is shorter than 20 mm, the cover sheet 8 may be easily twisted. If the draping length is longer than 100 mm, on the other hand, the cover sheet 8 may become so hard as to deteriorate the feeling of use of the napkin 1 resulting in a decrease in the underwear follow-up performance and permitting the absorbed fluid to leak out.

The above cantilever method is conducted as described below in compliance with the JIS-L1018. Namely, five pieces of the object to be measured having a length of 150 mm and a width of 25 mm are overlapped one upon the other to obtain a measuring sample. Next, by using a cantilever manufactured by Daiei Kagaku Seiki Mfg. Co., the measuring sample is held under a holding plate of the cantilever and is slid in a tilted direction at a speed of 5 mm/sec to automatically measure a distance it has traveled. Measurements are taken in both of the cases of when the surface of the measuring sample faces down and when the back surface of the measuring sample is on the lower side, and an average value is regarded as the measured result.

The napkin 1 is fixed to the underwear as described below. Namely, the protection sheet 7 on the side of the back sheet 4 is removed, first. Next, the napkin 1 or the absorbing body 2 is fixed to the underwear via the sticking portion 6. The top sheet 3 is covered with the cover sheet 8 and is prevented from being fouled.

Next, the central region 8C of the cover sheet 8 is broken along the sectionalizing line 9. As a result, there are formed four flaps 10F, 10B, 10L and 10R that are separated from each other.

Next, as shown in FIG. 4, these flaps 10F, 10B, 10L and 10R are expanded, respectively. That is, the front flap 10F is expanded forward being folded in a folding region 14F along the front edge 2F, and the rear flap 10B is expanded rearward being folded in a folding region 14B along the rear edge 2B. Further, the left flap 10L is expanded toward the left being folded in a folding region 14L along the left edge 2L, and the right flap 10R is expanded toward the right being folded in a folding region 14R along the right edge 2R. As a result, the top sheet 3 is exposed.

Figure 5:
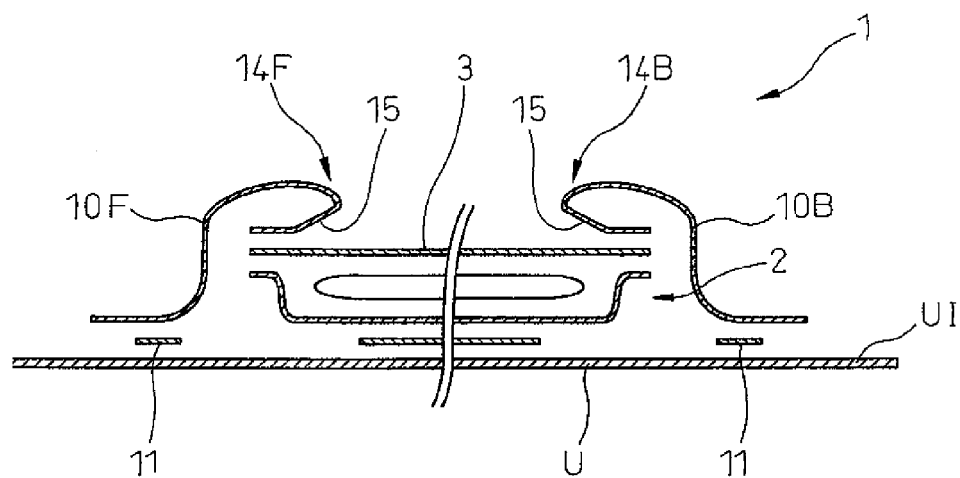
FIG. 5 is a schematic longitudinal sectional view of the sanitary napkin illustrating the state of use.
Figure 6:
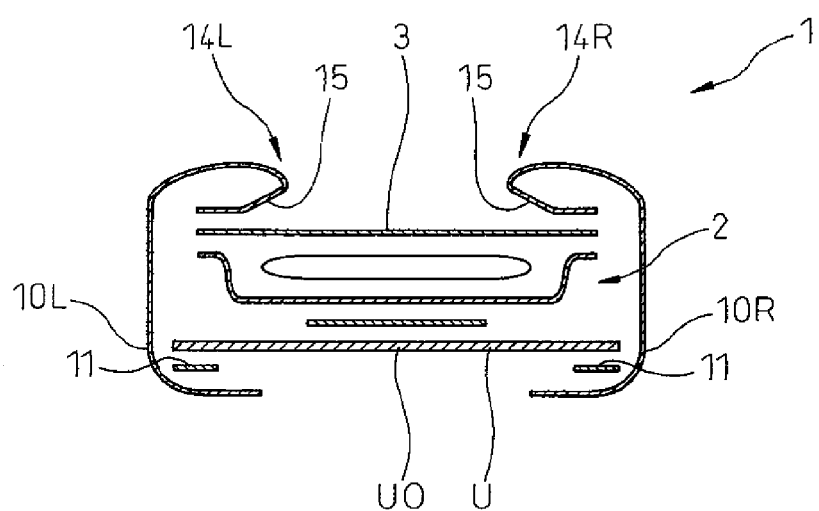
FIG. 6 is a schematic transverse sectional view of the sanitary napkin illustrating the state of use.

Next, the flaps 10F, 10B, 10L and 10R are attached to the underwear via the respective sticking portions 11. That is, as shown in FIG. 5 which is a longitudinal sectional view of the napkin 1, the front flap 10F is fixed to the inner surface UI of the underwear U in front of the absorbing body 2, and the rear flap 10B is fixed to the inner surface UI of the underwear U at the back of the absorbing body 2. As shown in FIG. 6 which is a transverse sectional view of the napkin 1, further, the left flap 10L and the right flap 10R are fixed to the outer surface UO of the underwear U under the absorbing body 2.

Thus, the flaps 10F, 10B, 10L and 10R are fixed to the underwear U and, therefore, the absorbing body 2 is fixed to the underwear U. In this case, the absorbing body 2 is fixed to the underwear U by both the flaps in the back-and-forth direction that are fixed being expanded in the back-and-forth direction like the front flap 10F and the rear flap 10B, and the flaps in the right-and-left direction that are fixed being expanded in the right-and-left direction like the left flap 10L and the right flap 10R. Further, the flaps fixed to the inner surface UI of the underwear like the front flap 10F and the rear flap 10B, are held sandwiched between the underwear U and the body of the user. On the other hand, the flaps fixed to the outer surface UO of the underwear U like the left flap 10L and the right flap 10R, work to hold the underwear U between these flaps and the absorbing body 2.

Despite external forces exerted on the absorbing body 2 from various directions, the absorbing body 2 can be suppressed from being twisted or deviated in position. Namely, the absorbing body 2 can be reliably fixed to the underwear U and, therefore, the absorbed fluid is suppressed from leaking. In addition, the user is liberated from the anxiety of leakage.

According to the embodiment of the invention, the front ends of the flaps fixed to the inner surface like the front flap 10F and the rear flap 10B are curved, suppressing pain or offensive feeling that may be caused when the front flap 10F and the rear flap 10B come in contact with the body of the user.

Further, non-sticking regions 13 are formed on the flaps 10F, 10B, 10L and 10R or, concretely, at their end portions, enabling the user to handle the flaps 10F, 10B, 10L and 10R by picking up the non-sticking regions 13. It is, therefore, allowed to easily fix the absorbing body 2 to the underwear U.

As will be understood from FIG. 4, the folding regions 14F, 14B, 14L and 14R are positioned on straight lines connecting the two neighboring ends of the sectionalizing line 9. As shown in FIG. 1, on the other hand, non-cut regions 8N are formed between the ends of the sectionalizing line 9 and the circumferential edge region 8P. As shown in FIGS. 5 and 6, therefore, the cover sheet 8 forms a leakage-preventing region 15 between the circumferential edge region 8P and the folded regions 14F, 14B, 14L and 14R or the flaps 10F, 10B, 10L and 10R, the leakage-preventing region 15 continuing over the whole circumference of the cover sheet 8. The leakage-preventing region 15 limits the fluid absorbed by the absorbing body 2 from flowing out and, therefore, works as a leakage-preventing wall along the surface of the top sheet 3.

In the embodiment of the invention, a piece of cover sheet 8 is simply joined to the absorbing body 2 to form the leakage-preventing region 15 that works as the leakage-preventing wall. Therefore, the leakage-preventing action can be easily obtained. The leakage-preventing region 15 has no seam. In addition, if the flaps 10F, 10B, 10L and 10R are pulled for fixing to the underwear U, the inner edge of the leakage-preventing region 15 rises from the top sheet 3, and the absorbed fluid is reliably trapped by the leakage-preventing region 15. This makes it possible to reliably suppress the leakage of the absorbed fluid.

The width of the circumferential edge region 8P is, desirably, 2 mm to 10 mm and, more desirably, 3 mm to 5 mm. This is because if the width of the circumferential edge region 8P is smaller than 2 mm, then the junction strength of the cover sheet 8 and the absorbing body 2 decreases. If the width of the circumferential edge region 8P is larger than 10 mm, the exposed surface of the top sheet 3 becomes small when the flaps 10F, 10B, 10L and 10R are expanded. Namely, if the top sheet is broadly exposed, leakage of the absorbed fluid can be suppressed even in case the position where the napkin 1 or the absorbing body 2 is fixed to the underwear U is deviated from the proper position to some extent.

On the other hand, the width of the non-cut regions 8N is, desirably, 2 mm to 10 mm and, more desirably, 3 mm to 5 mm. This is because if the width of the non-cut regions 8N is smaller than 2 mm, the tensile strength of the cover sheet 8 in the non-cut regions 8N decreases and, therefore, the leakage-preventing effect of the leakage-preventing region 15 decreases. If the width of the non-cut regions 8N is larger than 10 mm, the exposed surface of the top sheet 3 becomes small when the flaps 10F, 10B, 10L and 10R are expanded.

Next, another embodiment of the invention will be described.

According to another embodiment of the invention, the regions surrounding the sticking portions 11 in the flaps 10F, 10B, 10L and 10R have a rigidity larger than the rigidity of other regions.

That is, in the embodiment shown in FIG. 7, an embossed region 20 is provided surrounding the sticking portions 11. The remaining region 21, however, is not embossed. In an embodiment shown in FIGS. 8A and 8B, on the other hand, an additional sheet 22 is joined surrounding the sticking portions 11. The additional sheet 22, however, is not joined to the remaining region 21.

This makes it easy to handle the flaps 10F, 10B, 10L and 10R. Therefore, the flaps 10F, 10B, 10L and 10R can be easily fixed to the underwear U.

Here, it is desired that the ratio occupied by the embossed region 20 or the additional sheet 22 to the whole of the flaps 10F, 10B, 10L and 10R is not less than 10% and is, particularly, 40% to 100%.

In the embodiment shown in FIG. 7, if the embossed region 20 is of a rugged pattern, the contact area can be decreased between the flaps 10F, 10B and the body of the user, preventing stuffiness and improving touch feeling. This, further, excels in transferring the hot-melt adhesive of when the sticking portions 11 are joined to the flaps 10F, 10B, 10L and 10R.

Figure 8A:
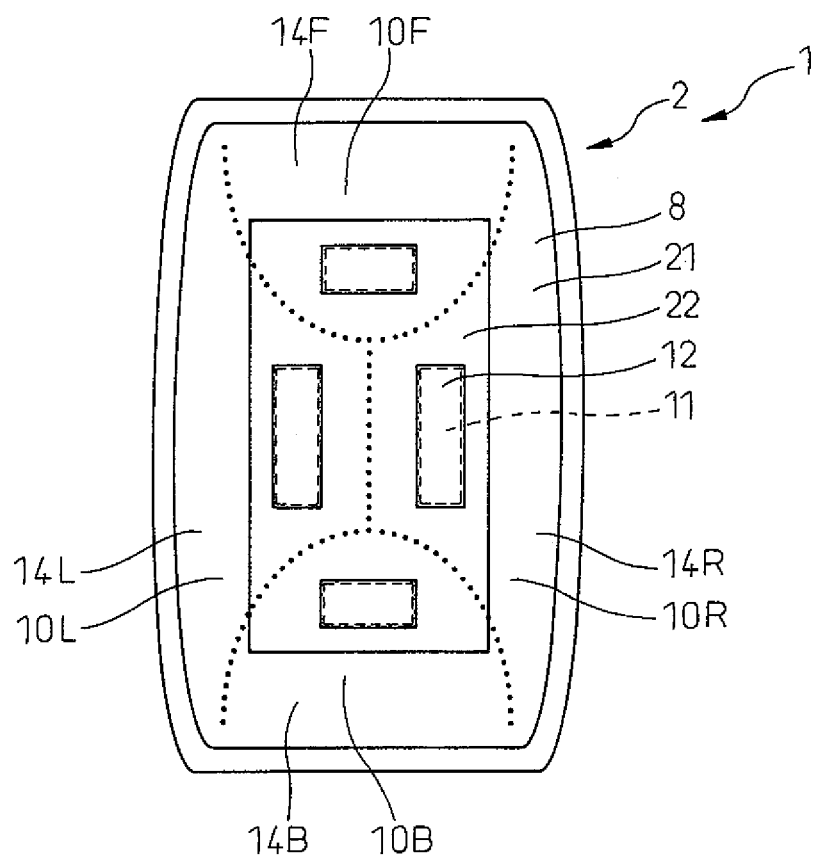
FIG. 8A is a front view of the sanitary napkin according to a further embodiment of the invention.
Figure 8B:
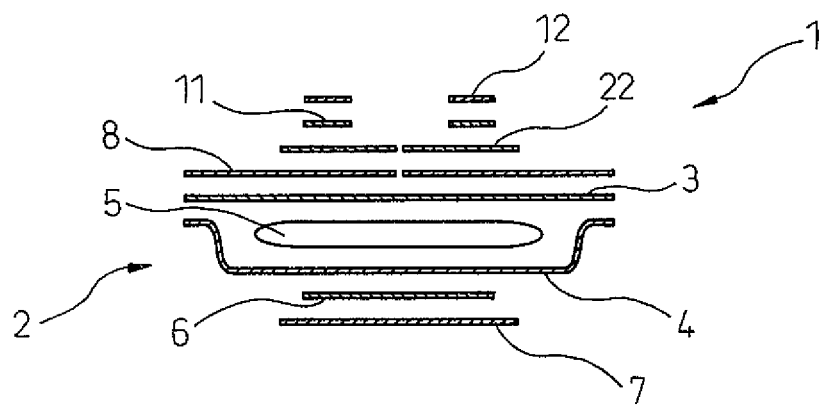
FIG. 8B is a schematic transverse sectional view of the sanitary napkin according to a further embodiment of the invention.

In the embodiment shown in FIGS. 8A and 8B, further, the additional sheet 22 may be of, the same material as the cover sheet 8, or may be of the other material. Further, the additional sheet 22 may be joined to the back surface of the cover sheet 8. A hot-melt adhesive or the like is used for joining the additional sheet 22. The sectionalizing line is formed after the additional sheet 22 is joined to the cover sheet 8 and is, therefore, formed in the additional sheet 22, too.

In the embodiments shown in FIG. 7 and FIGS. 8A and 8B, the sticking portions 11 are covered with separate protection sheets 12. However, a common protection sheet 12 may be provided, as a matter of course.

In other words, this means that in the embodiments shown in FIG. 7 and FIGS. 8A and 8B, the remaining region 21 inclusive of the folding regions 14F, 14B, 14L and 14R has a rigidity smaller than the rigidity of the embossed region 20 or the region to where the additional sheet 22 is joined. As a result, the flaps 10F, 10B, 10L and 10R can be easily folded and expanded.

Figure 9A:
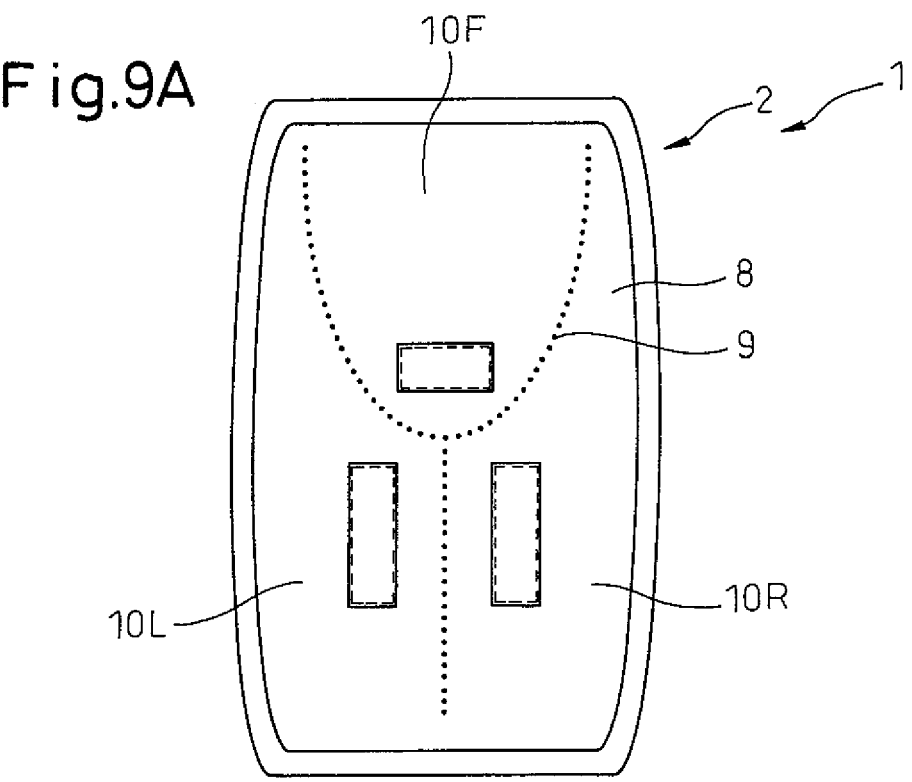
FIGS. 9A and 9B are front views of the sanitary napkin showing alternative embodiments of the sectionalizing lines.
Figure 9B:
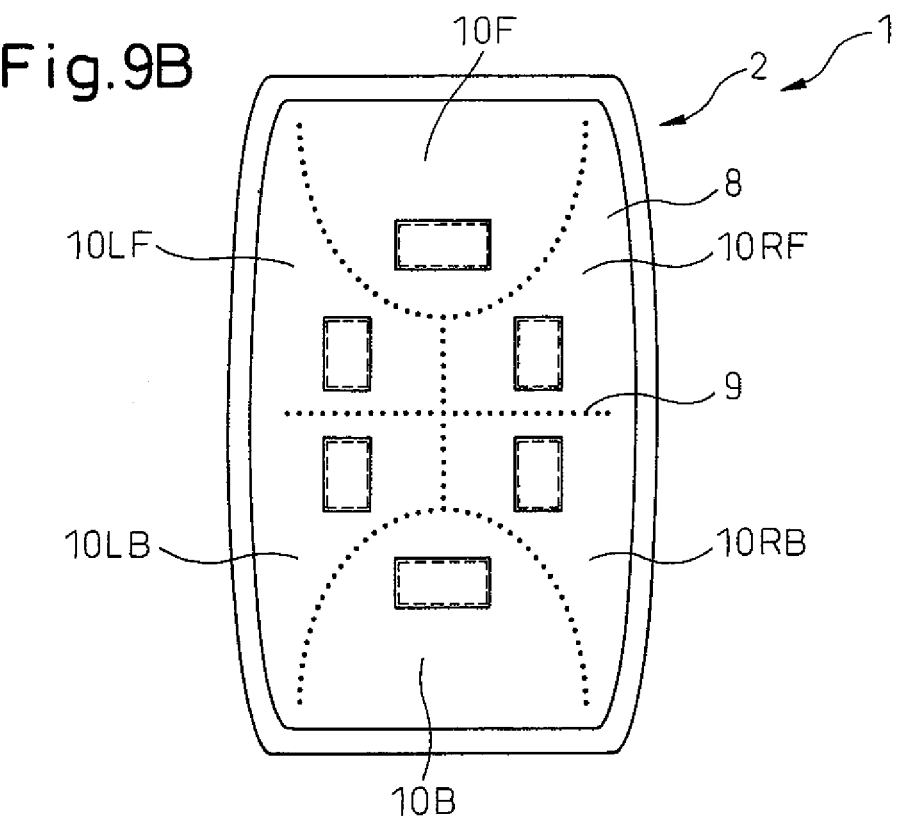

In the foregoing description, the sectionalizing line 9 is so formed that four flaps are sectionalized in the central region 8C of the cover sheet 8. However, the number of the flaps may not have to be four. That is, as shown in FIG. 9A, the sectionalizing line 9 may be so formed as to sectionalize three flaps 10F, 10L and 10R in the central region 8C or, as shown in FIG. 9B, the sectionalizing line 9 may be so formed as to sectionalize six flaps 10F, 10B, 10LF, 10LB, 10RF and 10RB in the central region 8C.

Generally speaking, therefore, at least three flaps are sectionalized by the sectionalizing line 9 in the central region 8C of the cover sheet 8.

Figure 10:
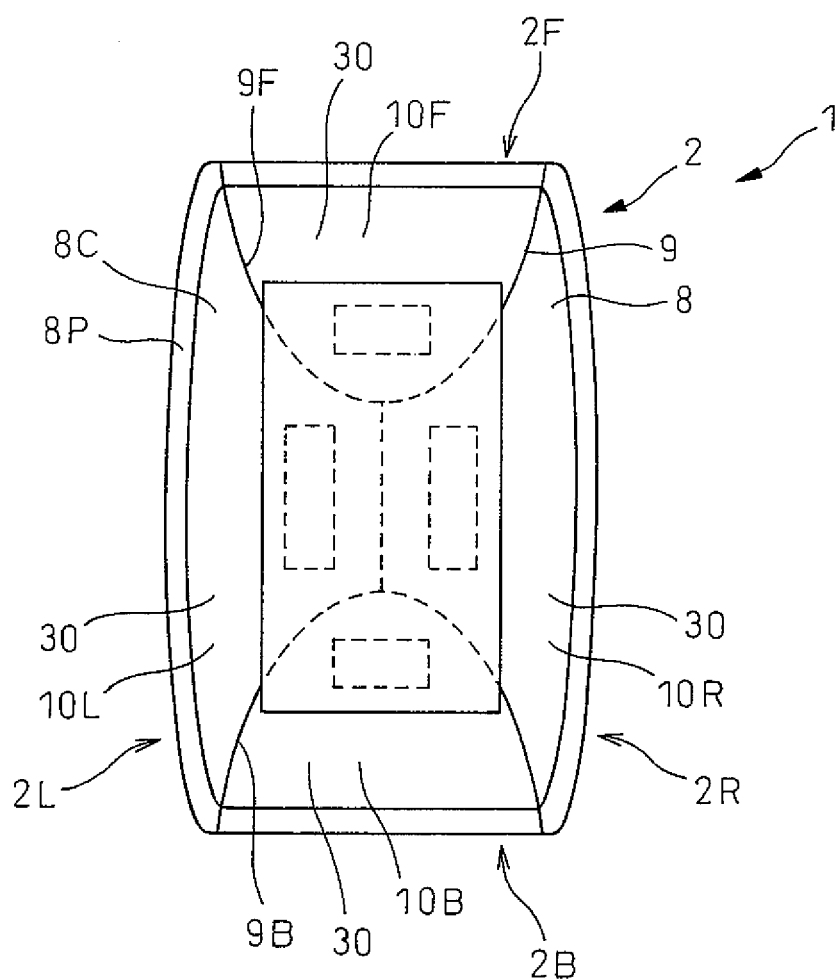
FIG. 10 is a front view of the sanitary napkin showing an alternative embodiment of the cover sheet.

In the foregoing description, further, the cover sheet 8 is constituted by a piece of sheet. The cover sheet 8, however, can be constituted by a plurality of pieces of separate cover sheet portions. Namely, in an embodiment shown in FIG. 10, the cover sheet 8 is constituted by, for example, four pieces of cover sheet portions 30. In this case, the cover sheet portions 30 cover portions of the surface of the top sheet 3; i.e., the cover sheet portions 30 as an entire cover substantially the entire surface of the top sheet 3. Further, the sectionalizing lines 9 formed among the neighboring cover sheet portions 30 extend traversing the circumferential edge region 8P. In the embodiment shown in FIG. 10, further, the cover sheet portions 30 are forming the flaps 10F, 10B, 10L and 10R, respectively. However, the plurality of flaps 10F, 10B, 10L and 10R may be formed by a piece of cover sheet portion 30. Further, the cover sheet portions 30 may be overlapped one upon the other.

REFERENCE SIGNS LIST 1 sanitary napkin
2 absorbing body
3 top sheet
4 back sheet
5 absorber
8 cover sheet 8C central region
8P circumferential edge region
9 sectionalizing line
10F front flap
10B rear flap
10L left flap
10R right flap
11 sticking portions
13 non-sticking portions
14F, 14B, 14L, 14R folding regions
15 leakage-preventing region
20 embossed region
21 remaining region
22 additional sheet

The invention claimed is:

1. An absorbent article comprising an absorbing body, the absorbing body including a fluid-permeable top sheet, a fluid-impermeable back sheet, and an absorber arranged between the top sheet and the back sheet, and a sticking portion being provided on the back sheet,
 wherein the absorbent article further comprises a cover sheet for covering substantially the entire surface of the top sheet,
 wherein a circumferential edge region of the cover sheet is joined to the absorbing body, and, in a central region of the cover sheet, a plurality of flaps, including at least one front or rear flap and one right and one left flap, for fixing the absorbing body to clothing are sectionalized by a sectionalizing line which is constituted by weakened lines or cut lines, wherein the weakened lines or cut lines have a configuration that defines the at least one front or rear flap and includes an apex and a weakened line or cut line that intersects the apex so as to define the right and left flaps,
 wherein, at the time of use, the plurality of flaps are folded in folding regions and are expanded so as to be fixed to the clothing,
 wherein the at least one front flap and rear flap that is folded in the folding regions along front or rear edges of the absorbing body and expanded in a back-and-forth direction so as to be fixed to an inner surface of the clothing, and the left and right flaps that are folded in the folding regions along left and right side edges of the absorbing body and are expanded in a right-and-left direction so as to be fixed to an outer surface of the clothing,
 wherein fixing portions for fixing the plurality of flaps to the clothing are attached to the plurality of flaps, and
 wherein the absorbing body is fixed to the clothing by the fixing portions on the flaps and sticking portion on the back sheet.

2. The absorbent article according to claim 1, wherein the sectionalizing line is so formed as to curve an end of the at least one front or rear flap.

3. The absorbent article according to claim 2, wherein flap regions surrounding the fixing portions have a rigidity larger than the rigidity of remaining flap regions.

4. The absorbent article according to claim 2, wherein the fixing portions for fixing the flaps to the clothing are attached to the plurality of flaps being separated away from the sectionalizing lines.

5. The absorbent article according to claim 2, wherein the cover sheet is fluid-impermeable.

6. The absorbent article according to claim 1, wherein flap regions surrounding the fixing portions have a rigidity larger than the rigidity of remaining flap regions.

7. The absorbent article according to claim 6, wherein the fixing portions for fixing the flaps to the clothing are attached to the plurality of flaps being separated away from the sectionalizing lines.

8. The absorbent article according to claim 6, wherein the cover sheet is fluid-impermeable.

9. The absorbent article according to claim 1, wherein the fixing portions for fixing the flaps to the clothing are attached to the plurality of flaps being separated away from the sectionalizing lines.

10. The absorbent article according to claim 9, wherein the cover sheet is fluid-impermeable.

11. The absorbent article according to claim 1, wherein the cover sheet is fluid-impermeable.

\* \* \* \* \*